United States Patent

Bennett

[11] Patent Number: 5,269,752
[45] Date of Patent: Dec. 14, 1993

[54] METHOD OF EXTRACORPOREAL TREATMENT USING A KINK RESISTANT CATHETER

[76] Inventor: Laurence M. Bennett, 3903 Sidehill Path, Austin, Tex. 78731

[21] Appl. No.: 758,870

[22] Filed: Sep. 12, 1991

[51] Int. Cl.⁵ ............................................. A61M 1/00
[52] U.S. Cl. ..................................... 604/28; 604/53; 604/281; 604/282
[58] Field of Search .......................... 604/4–10, 604/28, 52, 53, 164, 239, 261, 264, 275, 281, 282, 49

[56] References Cited

U.S. PATENT DOCUMENTS

| | | | |
|---|---|---|---|
| 3,169,528 | 5/1963 | Knox | 604/281 |
| 4,129,129 | 12/1978 | Amrine | 128/214 |
| 4,173,981 | 11/1979 | Mortensen | 604/282 |
| 4,596,564 | 6/1986 | Spetzler et al. | 604/281 |
| 4,639,252 | 1/1987 | Kelly et al. | 604/282 |
| 4,680,029 | 7/1987 | Ranford et al. | 604/4 |
| 4,756,705 | 7/1988 | Beijbom et al. | 604/4 |
| 4,808,158 | 2/1989 | Kreuzer et al. | 604/49 |
| 4,863,441 | 9/1989 | Lindsay et al. | 604/280 |
| 4,920,980 | 5/1990 | Jackowski | 604/95 |
| 5,011,469 | 4/1991 | Buckberg et al. | 604/4 |

FOREIGN PATENT DOCUMENTS 0250891 1/1988 European Pat. Off. ............. 604/53

OTHER PUBLICATIONS

Sarns Inc/3M; "Venous Return Catheters"; 2 pages; Form No. 16088102.
Sarns Inc/3M; "Venoatrial Catheter"; 2 pages; Form No. 16088107.

Primary Examiner—C. Fred Rosenbaum
Assistant Examiner—Mark Bockelman
Attorney, Agent, or Firm—Nils H. Ljungman & Associates

[57] ABSTRACT

A method of extracorporeal treatment using a venous return catheter containing a stiffening member disposed therein is provided.

4 Claims, 5 Drawing Sheets

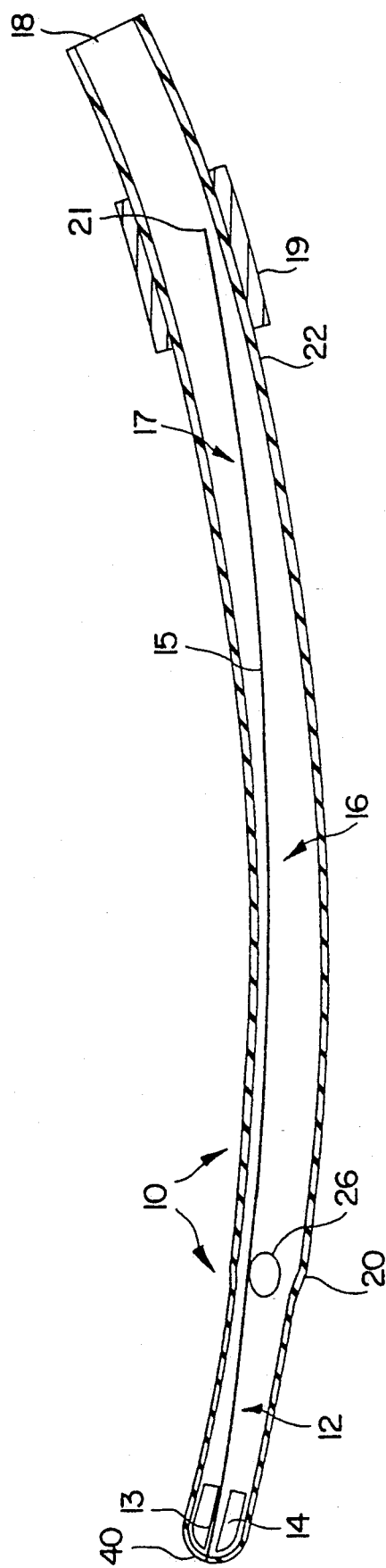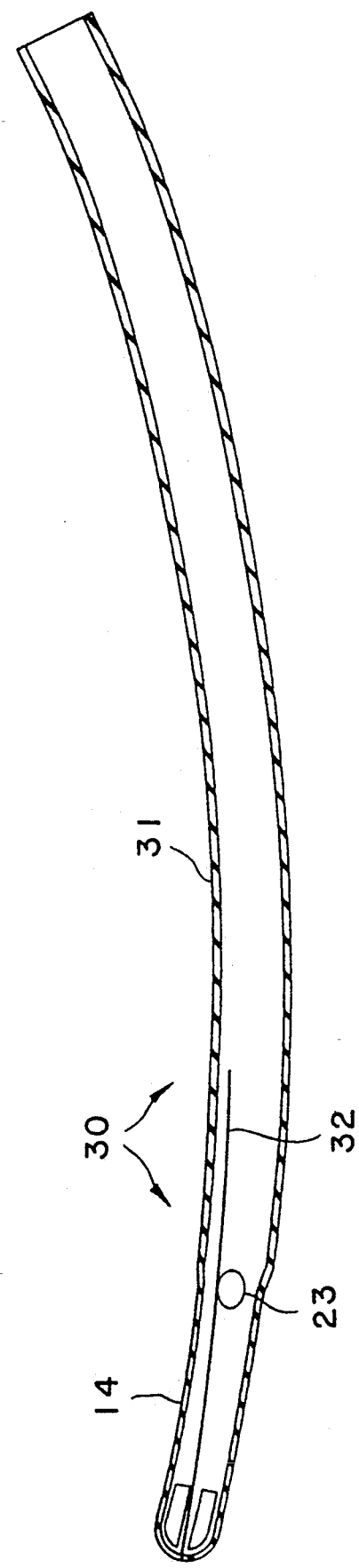

… …

METHOD OF EXTRACORPOREAL TREATMENT USING A KINK RESISTANT CATHETER

BACKGROUND OF THE INVENTION

1. Field of the Invention

The present invention relates to medical catheters and a method of using the same. In one particular aspect the present invention is suitable as a venous return catheter for draining fluid from a vena cava and, or from a right atrium of a heart into extracorporeal life support equipment.

2. Background Information

In many cases requiring heart surgery, the heart and lungs are routinely bypassed with their pumping and gas exchange functions being performed extracorporeally. Venous blood which is low in oxygen content and high in carbon dioxide is mechanically removed from the patient by medical catheters and connecting tubing. The tubing directs the venous blood to a pump and to a gas exchange device which is generally known as an oxygenator. Typically, there is also a heat exchanger incorporated in this circuit. After having carbon dioxide removed and oxygen added in the oxygenator and the temperature modified by the heat exchanger this, now, arterialized blood is returned to the patient by means of connecting tubing and medical catheters.

Medical catheters used to drain the venous blood are generally known as venous return catheters. U.S. Pat. Nos. 4,639,252; 4,129,129; 4,863,441 describe such catheters of single or dual drainage construction. These three patents address the extreme importance of maintaining an adequate flow of blood to supply the patient's needs during extracorporeal life support. Insufficient oxygen or excessive carbon dioxide can produce irreversible tissue damage in the patient while on heart-lung bypass.

U.S. Pat. No. 4,639,252 discusses surgical procedures which require manipulation of the heart which, as discussed, may result in a kinked venous return catheter. In the event that the venous return catheter becomes kinked, the flow to the life support apparatus will be significantly diminished or interrupted. The traditional means to resist kinking have been to make the wall of the catheter sufficiently thick and stiff to reduce the probability of kinking or to imbed coiled wire reinforcement into the wall of the catheter to resist kinking. The wall thickness has a large effect on the flow of a catheter because, according to Poiseuille's Law, flow varies with the fourth power of the inside diameter. Thick-walled catheters have the disadvantage of substantially reducing the flow for a given size catheter-insertion wound. After extracorporeal life support is completed, the catheter-insertion site must be repaired, which also is obviously also affected by the size of the catheter.

OBJECTS OF THE INVENTION

It is an object of the present invention to provide kink resistance by modifying the wall of the catheter so as to be able to reduce the size of the catheter wall in order to maximize blood flow therethrough.

Another principal object of the invention to reduce the cost of fabrication of venous return catheters.

Yet another principal object of the invention is to provide kink resistance in areas that are weakened by a plurality of inlet openings in the catheter.

A further object of the present invention is to facilitate the production of an array of various catheters having different elasticities and yield strengths so that the surgeon can specify the resistance to bending and permanent deformation characteristics closest to his needs.

Yet a further object of the present invention is to facilitate fabrication of a catheter having elasticity and yielding properties which vary along the length of the catheter.

An additional object of the present invention is to permit the use of soft flexible catheter material.

SUMMARY OF THE INVENTION

The present invention provides a thin-walled, kink-resistant venous return catheter and a method of using same. The kink-resistance is achieved by mounting a thin stiffening member in the lumen of the catheter. The catheter with stiffening provides adequate venous flow with a smaller overall cross-section thus reducing the size wound required for its insertion in the heart or vena cava.

In summary, one feature of the invention resides broadly in a method of bypassing blood flow from the heart during open heart surgery, those steps which comprise: (a) introducing a venous return catheter into the right atrium of the heart and extending the catheter into the inferior vena cava, (b) providing a thin stiffening member within the lumen of the catheter and rigidly fixed at one point, (c) utilizing a single lumen in the catheter to carry the blood flow from the inferior vena cava and the right atrium to extracorporeal life support equipment.

Another feature of the invention resides broadly in a method of bypassing blood flow from the heart during open heart surgery, those steps which comprise: (a) placing a venous return catheter into the vena cava, (b) providing a thin stiffening member within the lumen of the catheter and fixed at one point, (c) utilizing the catheter to carry the blood flow from the vena cava to extracorporeal life support equipment.

Yet another feature of the invention resides broadly in a method of bypassing blood flow from the heart during open heart surgery, those steps which comprise: (a) placing a venous return catheter into the right atrium, (b) providing a thin stiffening member within the lumen of the catheter and fixed at one point, (c) utilizing the catheter to carry the blood flow from the right atrium to extracorporeal life support equipment.

A yet further feature of the invention resides broadly in a kink-resistant medical catheter for use in the drainage of venous fluid during surgical procedures involving cardiopulmonary bypass, comprising: (a) a first diameter catheter portion forming the distal end of the catheter; said first diameter portion being suitable for placement within a vena cava, and said first diameter portion being provided with a plurality of drainage openings suitable for draining blood, (b) a second diameter catheter portion forming the proximal end of said catheter, said second diameter portion being in fluid communication with the first diameter portion having a larger diameter than the first diameter portion, said second diameter portion being provided with drainage openings suitable for draining blood, (c) a thin stiffening member portion within the lumen of the catheter and fixed at one point, (d) a transition catheter portion between the first and second diameter portions forming a smooth transition between said first and second diameter portions.

A still further feature of the invention resides broadly in a kink-resistant medical catheter for use in the drainage of venous fluid during surgical procedures involving cardiopulmonary bypass, comprising: (a) a tube generally comprising a cylinder having an insertion end portion and having at least one inlet opening and an outlet opening, (b) a thin stiffening member portion within the lumen of the catheter and fixed at one point.

BRIEF DESCRIPTION OF THE DRAWINGS

FIG. 1 is a transverse sectional view of a presently preferred embodiment of a kink-resistant venous return catheter, in a moderately bent condition, in accordance with the present invention.

FIG. 2 is a transverse sectional view of an alternate embodiment of the present invention with a helical coiled spring wire reinforced proximal section.

DESCRIPTION OF THE PREFERRED EMBODIMENTS

Figure 3:
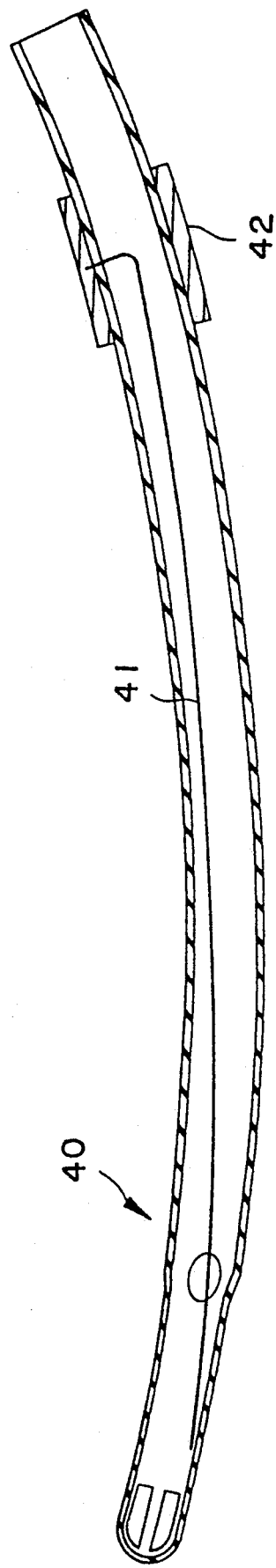
FIG. 3 is a transverse sectional view of an alternate embodiment of the present invention with the stiffening member retained at the proximal end.

Referring to the drawings, there is shown, in FIG. 1, a cross-sectional view of a preferred embodiment of the medical catheter 10 of the present invention. The medical catheter 10 is generally comprised of a first cross-sectional area portion 12, preferably generally comprising a cylinder, having an inlet opening or openings 13 and 14 through a cone-shaped distal end portion 40; a second, preferably larger cross-sectional area proximal end catheter portion 16, preferably generally comprising a cylinder, having an outlet opening 18; and a transition catheter portion 20, preferably generally comprising a frustum of a cone, and preferably disposed between the first and second catheter portions 12 and 16. The transition catheter portion 20 is in fluid communication with the first and second catheter portions 12 and 16 and may contain a plurality of inlet openings 26.

The first cross-sectional area catheter portion 12 is preferably dimensioned to be received within a vena cava, preferably the inferior vena cava, as shown in U.S. Pat. No. 4,129,129. The second, larger, cross-sectional area catheter portion is preferably dimensioned so as to be too large to be received within the vena cava.

As shown in FIG. 1, this embodiment of the catheter comprises a thin stiffening member 15 which is attached to and/or molded into the center of the distal end portion 40 and is otherwise free to move within the lumen 17 of the catheter 10. Reinforcing means 19 can be provided to prevent the free end 21 of the stiffening member 15 from penetrating the catheter wall 22.

The stiffening member 15 is supplied to resist kinking of the catheter 10 in the event that the catheter 10 is bent in use, for example, as noted in U.S. Pat. No. 4,639,252. The stiffening member 15 is permitted to freely float within the lumen 17 which results in the stiffness of the catheter 10 being symmetric around the long axis of the catheter 10. The stiffening member 15 allows the catheter wall 22 to be minimized in thickness thus allowing significantly greater flow for a given catheter 10 or allowing the use of a smaller catheter 10 for a given flow requirement. The reduction of the size of the catheter wall is a decided advantage over the catheters disclosed in U.S. Pat. Nos. 4,129,129, 4,639,252 and 4,863,441. A further advantage, as discussed above is the use of a smaller catheter which will obviously reduce the size of the wound made in the heart. The maximum pressure within the catheter 10 will rarely exceed 2 pounds per square inch thus the limit on the thinness of the catheter wall 22 is controlled by the forces exerted upon it by the suturing process, which hold it in place in the right atrium of the heart. Some deformation of the catheter wall 22 at the point of entry into the right atrium may be desirable to provide resistance to slippage or leakage.

It is desirable to utilize a soft flexible material for the catheter wall 22 in order to minimize tissue damage. However, utilizing such a soft material can allow the kinking of the catheter 10 during use. In the past, helical wire coil reinforcement imbedded within the catheter wall has been used to prevent kinking. The helical wire coil necessitates a thickened wall section and, moreover, is costly compared with the use of a single stiffening member 15, as in the present invention. Further, helical wire coil reinforcement cannot easily be incorporated within the wall at the point of the inlet openings 26. Traditionally, additional means of reinforcement were used to prevent kinking at the inlet openings 26. The present invention does not require additional means of reinforcement because the stiffening member 15 is unaffected by the inlet openings 26. The reduction in complexity achieved by eliminating the need for additional reinforcement means therefore, reduces the cost of manufacture and further adds to reliability of the catheter.

The stiffening member 15 is preferably comprised of a medical grade of stainless spring steel. It may be advantageous to soften about half the stiffening member 15 nearest the outlet 18 to allow the surgeon to semi-permanently form the catheter to its most unobtrusive position outside the heart and major vessels. The softening may be achieved by selectively annealing only the proximal part of the wire and leaving the remainder in its spring hardened condition. The stiffening member is preferably coated with a thin layer of flexible medical grade polymer such as polyvinyl chloride by the dip or spray coating method.

The distal end portion 14, the reinforcing means 19 and the proximal end portion 16 are preferably comprised of a medical grade of transparent polymer such as polyvinyl chloride or polyurethane. These polymers are typically in the hardness range of 40 to 90 on the Shore A scale. The distal end portion 14 is can be produced by the process of injection molding and the proximal end portion 16 by extrusion, either portion not being limited to either method of production. The transition portion 20 can be made by either of these methods or any other practical method. The distal end portion and the proximal end portion may be joined by means such as solvent bonding, radio frequency welding or cementing.

The embodiment of FIG. 2 shows a two-stage catheter 30 with a helical coiled wire reinforced proximal end portion 31 and a shortened stiffening member 32 in the distal end portion 14. The stiffening member provides kink resistance in the distal end portion 14 and particularly for the plurality of inlet openings 23.

The embodiment of FIG. 3 shows a two-stage catheter 40 which has the stiffening member 41 retained or attached at the proximal end by a two piece retainer and seal 42. This retainer and seal 42 can be made as one piece as well. In the embodiment shown in FIG. 3, the catheter is of one-piece construction preferably produced by the dip-molding process. The retainer and seal 42 can be made of rigid polymer such as polycarbonate and is preferably sealed to the catheter with cement or solvent bonding.

Figure 4:
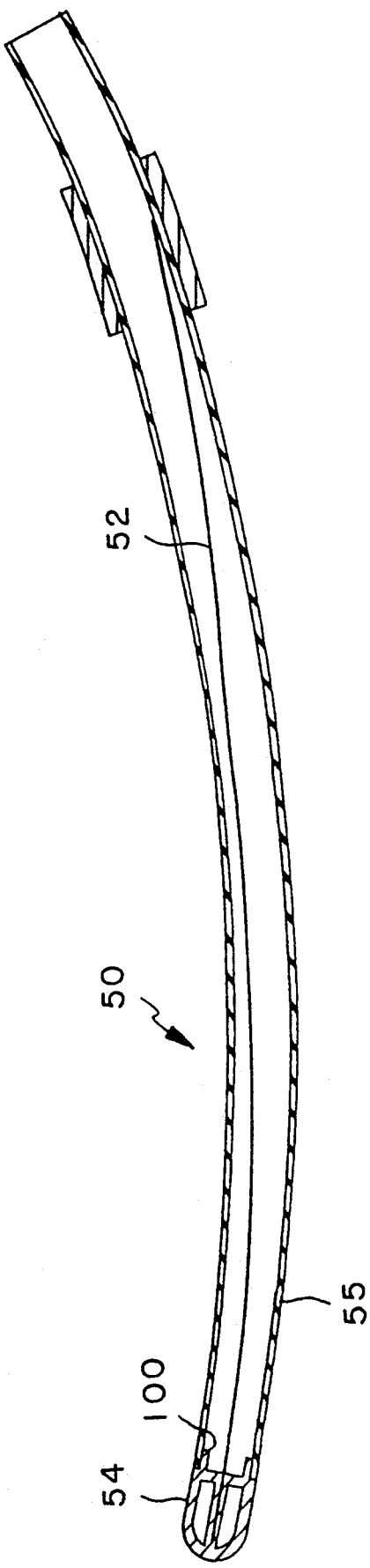
FIG. 4 is a transverse sectional view of the present invention where the catheter is of the single stage type.

The embodiment of FIG. 4 shows a single stage catheter 50 of generally constant diameter, the stiffening member 52 is fixed preferably by cementing or insert injection molding in the distal end portion 54. The distal end portion 54 is attached to the proximal end portion 55 preferably by means of solvent bonding, cementing or radio frequency welding, preferably at connection 100.

Figure 5:
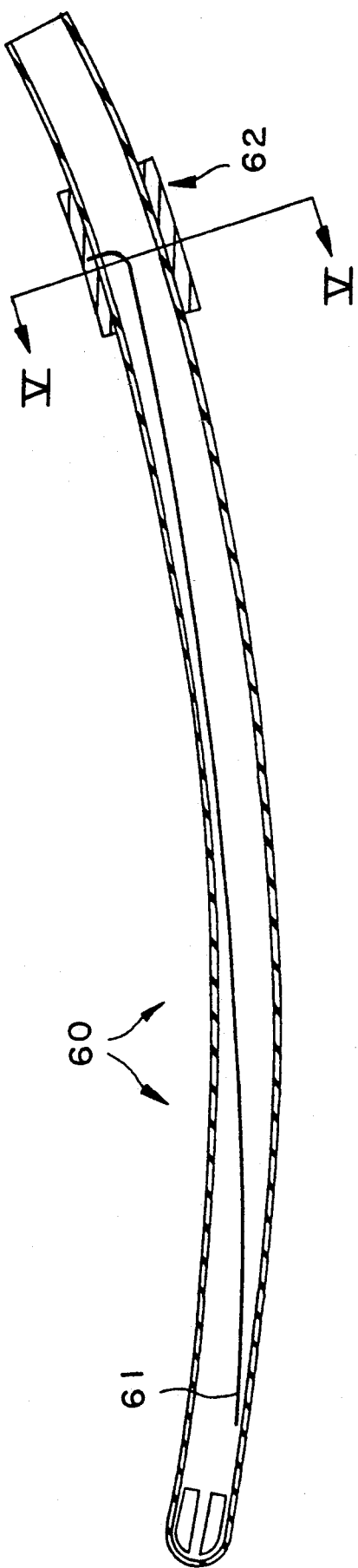
FIG. 5 is a transverse sectional view of the present invention where the catheter is of the single stage type and the stiffening member is retained at the proximal end.

The embodiment of FIG. 5 shows a single stage catheter 60 of generally constant diameter which as the stiffening member 61 retained at the proximal end by a two piece retainer and seal 62. In this embodiment the catheter is of one piece construction preferably produced by the dip-molding process.

Figure 5A:
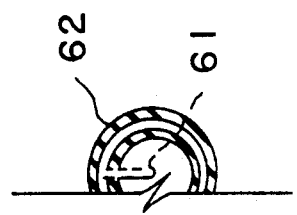
FIG. 5a is a cross-sectional view of the catheter taken along lines V—V of FIG. 5.

FIG. 5a shows a cross-sectional view of the catheter of FIG. 5 taken along lines V—V. The use of two-piece retaining and seal 62 is depicted showing the retention of stiffening member 61 therewithin.

Figure 6:
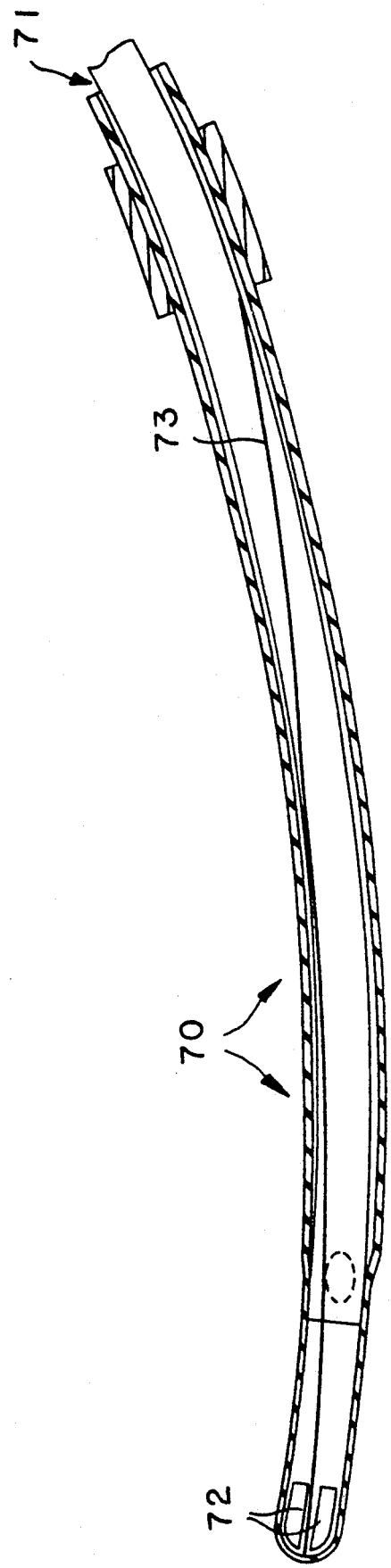
FIG. 6 is a transverse sectional view of the present invention with an installation obturator in place.

It is commonly known in the field of catheterization to minimize blood loss during insertion of the catheter. It may be desirable to utilize an obturator tube in the lumen of the catheter to restrict the flow of blood in the catheter until full insertion of the catheter is effected. FIG. 6 depicts the use of an obturator tube 71 inserted in catheter 70 so that the flow from inlet openings 72 is directed through the tube. Inlet holes 26, would then be closed so as to not permit blood from either entering or exiting through these holes. The stiffening member 73 is also contained within the obturator tube 71 and thereby does not impede the removal of the obturator tube 71 from the proximal end of the catheter 70.

Figure 7:
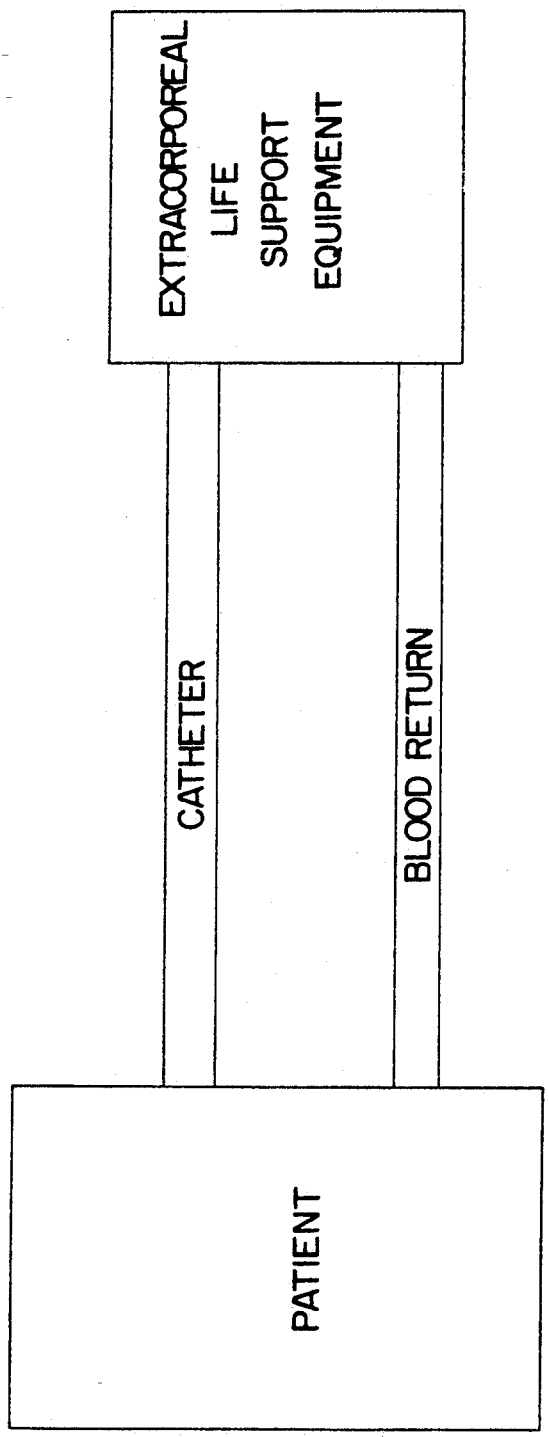
FIG. 7 is a schematic diagram showing the method of bypassing blood flow using the present invention.

FIG. 7 shows, in schematic form, the method of bypassing blood flow using the present invention.

All, or substantially all, of the components and methods of the various embodiments may be used with at least one embodiment or all of the embodiments, if any, described herein.

All of the patents, patent applications and publications recited herein, if any, are hereby incorporated by reference as if set forth in their entirety herein.

The details in the patents, patent applications and publications may be considered to be incorporable, at applicant's option, into the claims during prosecution as further limitations in the claims to patentably distinguish any amended claims from any applied prior art.

The invention as described hereinabove in the context of the preferred embodiments is not to be taken as limited to all of the provided details thereof, since modifications and variations thereof may be made without departing from the spirit and scope of the invention.

What is claimed is:

1. In a method of bypassing blood flow from the heart of a patient during open heart surgery, those steps which comprise:

(a) providing a thin stiffening member with a first end and a second end within a blood transmitting lumen passage of a venous return catheter;

said first end being rigidly fixed at one point to the blood transmitting lumen passage;

the thin stiffening member being located in the blood transmitting lumen passage and said first end being permanently bonded to said one point in the lumen passage of the catheter so as to allow the flow of blood around the stiffening member through the lumen passage and so as to remain in place during blood transmittal;

said thin stiffening member being free at the second end so that the second end may float within the lumen passage;

(b) introducing the venous return catheter into the right atrium of the heart and extending the catheter into the inferior vena cava;

(c) utilizing the blood transmitting lumen passage in the catheter to carry the blood flow from the inferior vena cava and the right atrium to extracorporeal life support equipment; and (d) returning the blood flow from the extracorporeal life support equipment to the patient.

2. In a method of bypassing blood flow from the heart of a patient during open heart surgery, those steps which comprise:

(a) providing a thin stiffening member, with a first end and a second end, within a blood transmitting lumen passage of a venous return blood transmitting catheter;

said thin stiffening member being rigidly fixed at said first end at one point within the lumen passage;

said thin stiffening member being located within the blood transmitting lumen passage and having said first end permanently bonded to the lumen passage of the catheter so as to allow the flow of blood around the stiffening member through the lumen passage and so as to remain in place during blood transmittal through the blood transmitting lumen passage;

said lumen passage comprising a lumen opening and a blood transmitting passage;

said thin stiffening member being free at the second end so that the second end may float within the lumen passage;

(b) introducing the venous return catheter into the vena cava;

(c) utilizing the blood transmitting lumen passage in the catheter to the blood flow from the vena cava to extracorporeal life support equipment; and (d) returning the blood flow from the extracorporeal life support equipment to the patient.

3. In a method of bypassing blood flow from the heart of a patient during open heart surgery, those steps which comprise:

(a) providing a thin stiffening member, with a first end and a second end, within a blood transmitting lumen passage of a venous return catheter;

said first end being rigidly fixed at one point within the lumen passage;

the thin stiffening member being located in the blood transmitting lumen passage and being permanently bonded to the lumen passage of the catheter so as to allow the flow of blood around the stiffening member through the lumen passage and so as to remain in place during blood transmittal;

said thin stiffening member being free at the second end so that the second end may float within the lumen passage;

said lumen passage comprising a lumen opening and a blood transmitting passage;

(b) introducing the venous return catheter into the right atrium of the heart;

(c) utilizing the blood transmitting lumen passage in the catheter to carry the blood flow from the right atrium of the heart to extracorporeal life support equipment; and (d) returning the blood flow from the extracorporeal life support equipment to the patient.

4. In a method of withdrawing fluid from the heart of a patient, those steps which comprise:

(a) providing wire shaped a thin stiffening member, with a first end and a second end, within a fluid transmitting lumen passage of a venous return catheter;

said first end being rigidly fixed at one point to the lumen passage;

said thin stiffening member being located within the fluid transmitting lumen passage and being permanently attached at said first end to the lumen passage of the catheter so as to allow the flow of fluid around the stiffening member through the lumen passage and so as to remain in place during fluid transmittal;

said thin stiffening member being free at the second end so that the second end may float within the lumen passage;

said lumen passage comprising a lumen opening and a fluid transmitting passage;

(b) placing the catheter into the heart of the patient; and (c) utilizing the lumen passage in the catheter with the thin stiffening member to carry the fluid from the heart of the patient to extracorporeal equipment.

* * * * *